United States Patent [19]

Marschner

[11] Patent Number: 4,534,962
[45] Date of Patent: Aug. 13, 1985

[54] SODIUM BICARBONATE SUSPENSION AS DEODORANT PRODUCT

[75] Inventor: Frank W. Marschner, Whitehouse Station, N.J.

[73] Assignee: Colgate-Palmolive Company, New York, N.Y.

[21] Appl. No.: 423,952

[22] Filed: Sep. 27, 1982

Related U.S. Application Data

[63] Continuation of Ser. No. 221,093, Dec. 29, 1980, abandoned.

[51] Int. Cl.³ .................. A61K 7/32; A61K 47/00
[52] U.S. Cl. ...................... 424/65; 514/770; 514/781
[58] Field of Search ........................... 424/65

[56] References Cited

U.S. PATENT DOCUMENTS

| | | | |
|---|---|---|---|
| 74,871 | 2/1868 | Wilson | 424/65 |
| 279,195 | 6/1883 | Ilocomb | 424/65 |
| 1,558,405 | 10/1925 | Smith | 424/65 |
| 2,145,583 | 1/1939 | Carlson | 424/65 X |
| 2,373,933 | 4/1945 | Weeks | 424/69 X |
| 2,602,042 | 7/1952 | Abbott | 424/65 |
| 3,152,181 | 10/1964 | Shapiro et al. | 424/65 X |
| 3,485,915 | 12/1969 | Gerstein et al. | 424/65 X |
| 4,126,679 | 11/1978 | Davy et al. | 424/66 |

FOREIGN PATENT DOCUMENTS

| | | | |
|---|---|---|---|
| 968469 | 2/1958 | Fed. Rep. of Germany | 424/68 |
| 762847 | 4/1934 | France | 424/69 |
| 1187607 | 3/1959 | France | 424/69 |
| 1236071 | 6/1960 | France | 424/69 |
| 406561 | 12/1943 | Italy | 424/69 |
| 26987 | of 1912 | United Kingdom | 424/362 |
| 908308 | 10/1962 | United Kingdom | 424/362 |

OTHER PUBLICATIONS

Pharmaceutical Formulas, 1947, vol. II, p. 152.
Martindale, The Extra Pharmacopoeia, pp. 1705–1708, 1972.
Amer. Perfumes & Cosmetics, 10/1963, vol. 78, pp. 95–97.
Ash, A Formulary of Cosmetic Preparations, 1977, pp. 6, 11, 13, 14, 20, 24 and 25.

*Primary Examiner*—Dale R. Ore
*Attorney, Agent, or Firm*—Herbert S. Sylvester; Murray M. Grill; Norman Blumenkopf

[57] ABSTRACT

A novel stable pituitous bicarbonate suspension in an aqueous/alcoholic medium having a high alcohol content and a low water content, with substantially no bicarbonate in solution, containing hydroxyethyl cellulose as the essential suspending agent, said alcohol content exceeding the upper solubility of hydroxyethyl cellulose in said alcohol and the water content being sufficient to prevent precipitation of said suspending agent and at least 5% by weight; having utility in deodorant products such as roll-ons, pumps and on substrates such as deodorant pads. The concentration of sodium or potassium bicarbonate is preferably high, about 10%, however 1–20% may be used. The alcohol utilized herein is monohydric such as ethanol, methyl or isopropyl alcohol, however, a polyhydric alcohol such as propylene glycol, glycerine and/or polypropylene glycols may be partially substituted for the monohydric alcohol. The bicarbonate suspensions have been found to be less irritating to the body and dry faster than the bicarbonate solutions because the bicarbonate is delivered as a powder to be activated by body moisture.

10 Claims, No Drawings

SODIUM BICARBONATE SUSPENSION AS DEODORANT PRODUCT

This is a continuation of application Ser. No. 221,093, filed Dec. 29, 1980, now abandoned.

The present invention relates to stable pituitous suspensions of sodium or potassium bicarbonate in aqueous/predominantly alcoholic media containing hydroxyethyl cellulose as the essential suspending agent, having particular utility in personal care deodorant products such as roll-ons, pumps, lotions and on various substrates such as deodorant pads.

BACKGROUND AND PRIOR ART

Sodium bicarbonate has long been recognized for its deodorant properties, and has commonly been used as a deodorant in refrigerators. In addition, plain powdered sodium bicarbonate or diluted with talc, cornstarch, rice-flour, or other filler has been used as an underarm deodorant as disclosed in the Journal of Investigative Dermatology Vol. 71946 pages 131-133 and U.S. Pat. No. 279,195 and No. 1,558,405.

Aqueous ethanol solutions of sodium or potassium bicarbonate as deodorant products have also been disclosed in British Pat. No. 1,553,739. Although said bicarbonate solutions are efficacious deodorants, underarm irritation has been observed at the 10% level of potassium bicarbonate. It has also been found that aqueous or aqueous/alcoholic sodium bicarbonate solutions are pH unstable.

Aging studies have shown that the bicarbonate in solution breaks down liberating $CO_2$ and gradually converts into sodium carbonate (a known skin irritant). Bicarbonate solutions also have solubility limitations. Proportionately larger amounts of water are required for higher bicarbonate levels. Consequently less alcohol is permitted which results in wetter, slower drying products. Also, the preparation of sodium bicarbonate solutions above 6.9% are impossible due to its limited water solubility.

The prior art also discloses aerosol suspensions, dispensed via a pressurized container, containing sodium bicarbonate slurried with propellants in a 50:50 mixture in U.S. Pat. No. 2,959,225; and alkali metal bicarbonate in a 0.3 to 15% propellant-soluble vehicle such as ethanol with about 90% propellant in British Pat. No. 1,476,117. The difficulties and disadvantages encountered with aerosol suspensions of sodium or potassium bicarbonate discussed in aforesaid patents, include the settling and/or agglomeration of the dry particles, clogging of the dispensing nozzle, non-uniform spray of deodorant material, nonadherence of the bicarbonate deodorant to the sprayed area due to the bounce-off of said dry powder and/or too wet a spray resulting in too long a drying time, in addition to being detrimental to the environment.

Cosmetic sticks containing antiperspirants and/or sodium bicarbonate suspended in a solid vehicle of a water-insoluble alcohol, such as cetyl alcohol and a silicone oil, is disclosed in U.S. Pat. No. 4,126,679. The difficulty of using sodium bicarbonate in this stick is due to its decomposition into sodium carbonate at relatively low temperatures as clearly shown in this patent.

However, there is no disclosure of a stable pituitous sodium or potassium bicarbonate suspension in an alcoholic aqueous media containing hydroxyethyl cellulose as the essential suspending agent, which requires usually no shaking prior to use, which substantially differs from the prior art aqueous or aqueous alcoholic solutions, aerosol suspensions and solid stick suspensions.

SUMMARY OF THE INVENTION

The primary object of the invention is to solve existing disadvantages by providing a novel stable alcoholic aqueous pituitous bicarbonate suspension containing hydroxyethyl cellulose as the essential suspending agent which maintains said bicarbonate particles uniformly dispersed and suspended in said high alcohol, low water content media, and requires little or no shaking prior to use.

Another object of this invention is to provide a more efficacious and fast drying deodorant product containing high alcohol and high bicarbonate levels.

Still another object of this invention is to provide deodorant products which are less irritating to the body.

Another object of this invention is to deliver the sodium or potassium bicarbonate as a powder to be activated by body moisture.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the deodorant product of this invention comprises a fast drying, non-sticky, low irritating alkali metal bicarbonate pituitous suspension in a vehicle comprising at least about 50% lower aliphatic monohydric alcohol, at least about 5% and up to about 25% water and hydroxyethyl cellulose as the essential suspending agent.

More specifically, present invention relates to stable pituitous suspensions of about 1-20% and preferably at least 5% sodium or potassium bicarbonate suspended in an alcoholic/aqueous media with essentially little or no bicarbonate in solution. This combination of high bicarbonate and high alcohol levels results in very effective fast drying non-irritating deodorant products. Said deodorant products evaporate rapidly leaving either a white (Baking Soda) residue or invisible film on the skin. The latter is achieved by adding non volatile polar or non-polar ingredients to the formula such as polyhydric alcohols or emollient oils.

It has been found that alcoholic/aqueous bicarbonate suspensions are highly desirable in aesthetics and superior to bicarbonate solutions. Bicarbonate solutions have been observed to cause skin irritation whereas bicarbonate suspensions are essentially non-irritating to the armpit. It has been discovered that aqueous or aqueous/alcoholic Sodium Bicarbonate solutions are pH unstable in aging studies. Bicarbonate in solution breaks down liberating $CO_2$ and gradually converts into sodium carbonate (a known skin irritant). Alcoholic/aqueous bicarbonate suspensions on the other hand are pH stable thus explaining the non-irritating properties of this type product. It is also believed that Bicarbonate powder in suspension products can be control released by the addition of water insoluble ingredients which form a more water resistant film on dryout. This type of controlled release can further reduce the risk of skin irritation which cannot be achieved with aqueous/alcoholic bicarbonate solutions.

Skin irritation problems experienced with bicarbonate solutions can be explained as bicarbonate instability and its conversion into an irritating carbonate salt. Three products were made using 5% sodium bicarbonate as follows and examined for pH over a short aging period at 120° F.

|  | A<br>Water<br>Soln. | B<br>Water/Alcohol<br>Soln. | C<br>Alcohol/Water<br>Suspension |
|---|---|---|---|
| Distilled Water | 95.0 | 80.0 | 15.0 |
| Sodium Bicarbonate | 5.0 | 5.0 | 5.0 |
| SD 40 Ethanol | — | 15.0 | 79.6 |
| Hydroxyethyl | — | — | 0.4 |
| Cellulose | 100.0 | 100.0 | 100.00 |
| | | pH (1:9 Parts Distilled Water) | |
| Initial pH (After Making) | 8.6 | 8.7 | 8.62 |
| 4 days at 120° F. | 9.5 | 9.5 | 8.6 |
| 17 days at 120° F. | 9.9 | 9.9 | 8.6 | pH data shows the instability of both bicarbonate solutions and the superior stability of the suspension product. Bicarbonate in solution gradually releases $CO_2$ and converts into the higher alkaline irritating carbonate salt.

$$2NaHCO_3 \rightarrow Na_2CO_3 + H_2O + CO_2 \uparrow$$

Formula (b) British Patent Specification No. 1,553,739 likewise showed pH instability at 120° F. and at ambient temperature.

| Natrosol 250 HR (hydroxyethyl cellulose) | 4.0 |
|---|---|
| Procetyl AWS (propoxylated cetyl alcohol) | 3.0 |
| Sodium Bicarbonate | 1.0 |
| Ethanol (SD 40) | 45.0 |
| Distilled Water | 47.0 |
| | 100.0 |
| pH (1:10 Parts Distilled Water) | |
| Initial pH (after making) | 8.8 |
| 124 hours later | — |
| Ambient Temperature | 9.4 |
| 120° F. | 9.95 |

Accordingly, an alcoholic/aqueous bicarbonate suspension deodorant offers many advantages and are unexpectedly superior to a bicarbonate solution deodorant product as evidenced by pH stability, non-irritating to the skin, fast drying properties, maximum deodorant protection and unlimited bicarbonate levels. Unlike bicarbonate solutions, bicarbonate in a suspension product is released by sweat secretion and the addition of water insoluble ingredients can further control and retard the release of bicarbonate under the armpit. In addition, a smooth, dry (talcum type) powder feel or smooth, non-gritty invisible film (with emollients) or white film (bicarbonate alone) is left on the skin.

The alcoholic/aqueous bicarbonate suspensions of this invention require a suspending agent, otherwise bicarbonate particles will settle and cake at the bottom of the container and cannot be adequately dispersed with shaking. Compounds used principally for thickening would slow down the settling rate, but offer no solution against compacting. Moreover, thickeners would in fact restrict the shaking motion for uniform particle redistribution. Suspending agents when used effectively prevent compacting of the bicarbonate particles and permit a uniform dispersion when shaken. The ideal suspension is one which requires essentially no shaking and where the particles remain uniformly suspended as exemplified in this invention.

Stable aqueous/alcoholic suspensions are usually difficult to prepare. An organoclay mineral product has been successfully employed in making bicarbonate suspensions, but the products usually require vigorous shaking before use.

However, it has been found that hydroxyethyl cellulose, which is a water soluble polymer, provides unique suspending properties to alkali metal bicarbonate in aqueous/high alcohol media. Although, hydroxyethyl cellulose is normally considered a thickener for aqueous type systems, it has been found to have unusual suspending properties in high alcohol/aqueous systems. Such suspensions are stringy and pituitous and offer superb suspending properties. This suspending agent gives exceptionally stable pituitous suspensions with no bicarbonate segregation after two weeks at 40° F., ambient or 110° F. temperature conditions, and require no shaking before use. This unexpected property of forming a stable pituitous bicarbonate suspension in a high alcohol/low water containing media is not possessed by other cellulosic derivatives such as hydroxypropyl cellulose, sodium carboxymethyl cellulose, hydroxypropylmethyl cellulose (Methocel) and other water soluble polymers.

In addition to the hydroxyethyl cellulose which is the essential suspending agent, it may be optionally desirable to use fumed silica (Cab-O-Sil) in combination with the hydroxyethyl cellulose. The hydroxyethyl cellulose per se constitutes about 0.1–1% and the fumed silica constitutes about 0.1–1%, and the total amount is preferably about 0.9–2% by weight of the total composition.

The alkali metal bicarbonate suspended in the alcoholic/aqueous vehicle will generally be sodium bicarbonate or potassium bicarbonate. It has been found that high levels of bicarbonate, in excess of 6.9% can not be readily dissolved in an aqueous/alcoholic media. However, because of the desirability of higher levels of bicarbonate, suspensions thereof with the aid of suitable suspending agents can be formulated into stable alcoholic/aqueous media. It is preferable to use micropulverized sodium or potassium bicarbonate powder, having a particle size of about 5 to 100 microns and preferably 10 to 25 microns. The smaller the particles, the easier it is to suspend in the vehicle, and the resultant product affords a non-gritty, smooth feel upon application to the skin. However, encapsulated bicarbonate powder either straight or in liquid or solid suspension may also be utilized. Although, bicarbonate suspensions have essentially no concentration limitations and can be used at any efficacious level desired, about 1–20% alkali metal bicarbonate is used and preferably 5–10% by weight.

Other deodorant ingredients such as zinc ricinoleate can be combined with the alkali metal bicarbonate, either in solution or in suspended form.

The vehicle into which the bicarbonate is suspended comprises an alcoholic aqueous media, said alcohol being a monohydric alcohol which is a lower alkanol such as ethanol, isopropyl alcohol or methanol. Polyhydric alcohols can be partially substituted for the monohydric alcohol, not to exceed the monohydric alcohol content. Suitable polyhydric alcohols include glycerine, propylene glycol and butylene glycol and polyglycols thereof. The monohydric alcohol content such as ethanol must exceed the upper solubility level for the water soluble polymer hydroxyethyl cellulose, in ethanol. The reported upper solubility level of this water soluble polymer in ethanol is 70%. Below this level and within normal soluble use ranges, a uniformly viscous liquid is obtained which pours evenly. Although, it appears aesthetically desirable, it will not support suspended powder and segregation occurs. However, at ethanol concentrations above its solubility range, the polymer becomes less soluble and forms the desired pituitous type liquid. If ethanol is further increased resulting in very low water levels the polymer will precipitate out and its suspending properties are again lost. Accordingly, a 70:30 ratio of ethanol:water is optimum. However, it was found that this problem can be eliminated by the sufficient addition of a polyhydric alcohol such as propylene glycol or glycerine. Accordingly, it has been found that the monohydric alcohol constitutes about 55–75%; and the water content may be as low as 5% if at least 10% polyhydric alcohol is also present in the suspension. The combined water and polyhydric alcohol content is at least about 15% and may be up to about 30%, whereas the water content per se may be up to about 25%. Thus, it is apparent that the proportions of monohydric alcohol, water and polyhydric alcohol are interdependent.

Bicarbonate suspension products have essentially no concentration limitations and can be used at any efficacious level desired. However, suspensions do have water limitations and require higher alcohol to water ratios to salt out the bicarbonate and prevent its solubility which would otherwise lead to bicarbonate instability.

The bicarbonate suspension deodorant products may also contain non-volatile polar or non-polar ingredients to effect the deposition of a dry, non-sticky invisible film on the skin upon evaporation, rather than a white bicarbonate residue. Said non-volatile agents include polyhydric alcohols such as glycerine, propylene glycol and butylene glycol and polyglycols thereof, and emollient oils, such as wheat germ oil, and any other alcohol soluble oils including isopropyl myristate, isopropyl palmitate, other fatty esters, fatty amides, fatty alcohols, fatty ethers such as stearyl ether, ethoxylated fatty alcohols and acids. The amount of emollient present is minor, about 1–5%. It has been found that the presence of minor amounts of lipophilic agents such as oils, silicone, lecithin and waxes and/or water insoluble resins and polymers in this deodorant suspension product will control bicarbonate release under the armpit. It has been observed that the bicarbonate roll-on deodorant suspension containing the wheat germ oils and the stearyl ether oils form a water resistant film when dry which may explain the gradual release of bicarbonate under the armpit and reduce the risk of skin irritance. Test results have shown that most of the bicarbonate is released within 15 minutes with increasing amounts over 1 hour and 6½ hour periods showing time release characteristic of the dry film.

In addition to the essential components of the present composition, one may also include therein minor amounts of components such as perfumes, coloring agents, ultraviolet absorbers to enhance the color, and the like, so as to improve the aesthetic value and consumer acceptability. Salts or pH buffering agents can be dissolved or suspended in the bicarbonate alcoholic/aqueous suspension product if desired. Minor amounts of other ingredients which do not adversely affect the beneficial properties of instant composition may also be included.

Known bacteriostats may also be added, although the bicarbonate suspension is effective as a deodorant without the use of added bacteriostats.

The bicarbonate suspensions of present invention have found utility in personal care deodorant products, such as roll-ons, pumps, on substrates such as deodorant pads, foot and body lotions.

The method of making the stable pituitous bicarbonate suspensions of instant invention generally comprises combining a heated aqueous or aqueous/monohydric or polyhydric alcohol mixture containing hydroxyethyl cellulose suspending agent with a monohydric alcoholic dispersion of alkali metal bicarbonate which may contain a second suspending agent, and mixing until a thick stable pituitous, stringy suspension is formed. More specifically, a clear Part 1 viscous solution of hydroxyethyl cellulose is prepared by heating and mixing with water or a water containing mixture of monohydric or polyhydric alcohol to a temperature of about 130°–140° F. A Part 2 preferably homogenized dispersion of alkali metal bicarbonate in a monohydric alcohol with or without a suspending agent is added with mixing to Part 1 viscous mixture to form a thick uniform, pituitous, stringy suspension wherein the solid particles of bicarbonate are uniformly suspended and remain in suspension. The perfume, colorants, emollients and other optional ingredients may be added to the alcoholic bicarbonate dispersion prior to its addition to the aqueous/alcoholic viscous hydroxyethyl cellulose solution, or subsequent thereto. The final suspension as well as each of the two dispersions independently, is preferably homogenized to effect a homogeneous final thick, pituitous suspension product.

Another method of making the stable pituitous bicarbonate suspensions comprises the sequential addition of the ingredients to a heated solution (about 140° F.) of water and alcohol, with agitation and/or homogenization. More specifically, the hydroxyethyl cellulose is added to the warm aqueous/alcoholic solution, followed by the monohydric alcohol followed by another suspending agent is desired, followed by the bicarbonate, followed by the perfume, color and any other optional ingredient. This method yields a thinner suspension than when utilizing the aforementioned two part method. Either method however, requires the initial preparation of a viscous aqueous containing hydroxyethyl cellulose solution prior to the addition of final amounts of monohydric alcohol. Accordingly, the order of addition and the preparation methods are important in achieving the desired pituitous suspension.

DETAILED DESCRIPTION OF THE INVENTION

The following specific examples are further illustrative of the present invention, but it is understood that the invention is not limited thereto. All amounts of various ingredients are by weight unless otherwise specified.

EXAMPLES 1-4

| | 1 | 2 | 3 | 4 |
|---|---|---|---|---|
| Part I | | | | |
| Deionized Water | 15.00 | 15.00 | 5.00 | 15.00 |
| Propylene Glycol | — | 10.00 | 10.00 | — |
| SD 40 Ethanol | 10.00 | — | — | 15.00 |
| Natrosol 250 HR[1] | 0.40 | 0.40 | 0.40 | 0.40 |
| Part II | | | | |
| SD 40 Ethanol | 63.15 | 60.65 | 70.65 | 56.10 |
| Cab-O-Sil[2] | 0.50 | 0.50 | 0.50 | 0.50 |
| Sodium Bicarbonate (Micropulverized) | 10.00 | 10.00 | 10.00 | 5.00 |
| Zinc Ricinoleate | — | — | — | 5.00 |
| Part III | | | | |
| Perfume | 0.50 | 0.50 | 0.50 | 0.50 |
| FD & C Green No. 3 (.1%) | 0.30 | 0.30 | 0.30 | — |
| D & C Green No. 8 (2.75%) | 0.15 | 0.15 | 0.15 | — |
| Arlemol E[3] | — | 1.50 | 1.50 | 1.50 |
| Wickenol 535[4] | — | 1.00 | 1.00 | 1.00 |
| | 100.0 | 100.0 | 100.0 | 100.0 |
| pH 1% aqueous Solution | 8.45 | — | — | 7.8 |
| Appearance | Thick, viscous pituitous suspension | Thick, viscous pituitous suspen. | Thick, viscous pituitous suspen. | Lotion-consistency pituitous suspension |

[1] Natrosol 250 HR: Hercules Inc., Hydroxyethyl Cellulose
[2] Cab-O-Sil: Cabot Corporation, Fumed Silica
[3] Arlemol E: I.C.I. American Inc., Polyoxypropylene Stearyl Ether
[4] Wickenol 535: Wickhen Products Inc., Wheat Germ Glycerides Example 1 drys rapidly to a smooth dry non-sticky white powder on the skin.

Examples 2, 3, 4 dry to a smooth dry non-sticky invisible film on the skin.

All examples show no Baking Soda or liquid separation on standing and require no shaking before use, and are non-irritating to the skin.

Aging tests over a period of two weeks at room temperature, 40° F. and 110° F. showed no bicarbonate segregation.

PREPARATION OF EXAMPLES

Step 1
Part 1 (all examples)
Disperse Natrosol in either Ethanol or Propylene Glycol. Add water with constant mixing and heat to 130°-140° F. until a uniform clear viscous solution is formed.

Step 2
Part 2 (Example 1-3)
Disperse Cab-O-Sil in alcohol and add Baking Soda gradually with rapid mixing. Homogenize until uniform.
(Example 4)
Dissolve Zinc Ricinoleate in warm Ethanol. Add Baking Soda and Cab-O-Sil and mix. Homogenize until uniform.

Step 3
Add Part 2 to Part 1 with mixing (thick pituitous stringy suspension is formed).

Step 4
Part 3
Admix all ingredients with Parts 1 and 2. Homogenize mixture into a thick uniform pituitous suspension.

EXAMPLE 5

| Ingredient | % |
|---|---|
| Propylene Glycol | 10.0 |
| Bentone Lt[1] | 0.5 |
| Deionized Water | 15.0 |
| Sodium Bicarbonate Micropulverized | 10.0 |
| SD 40 Ethanol | 64.5 |
| | 100.0 |

[1] Bentone LT: NL Industries Gellant is an organoclay material product designed for low molecular weight polar solvent/water systems and 100% water systems. It is a combination of hydroxyethyl cellulose and bentonite clay.

This example also forms a good uniform pituitous suspension since Bentone LT is a combination of hydroxyethyl cellulose and bentonite clay. This example shows the specificity of this specific suspending agent in the formation of a stable pituitous viscous suspension in accordance with the present invention.

PREPARATION OF EXAMPLE 5

1. Disperse Bentone LT in Propylene Glycol
2. Add water, mix and heat to 130°-140° F. until uniformly viscous.
3. Add Baking Soda—mix continuously.
4. Add alcohol, mix completely until uniform and homogenize.

EXAMPLE 6

Example 2 is repeated except that the stearyl ether and wheat germ glycerides are omitted and the ethanol content is increased to 63.15%. This product yields a stable uniform pituitous suspension of high viscosity from which the bicarbonate particles do not separate out upon standing but remain in suspension. This product, used in a roll-on container with a one-inch ball, gave good delivery and fast drying properties to form an invisible film on the skin.

EXAMPLES 7 AND 8

| Ingredient | Example 7 | Example 8 |
|---|---|---|
| Water | 37.65 | 37.65 |
| Propylene Glycol | 10.0 | 10.0 |
| Natrosol 250 HR | 0.4 | 0.9 |
| Ethanol | 37.65 | 37.65 |
| NaHCO₃ Micropulverized | 10.0 | 10.0 |
| Cab-O-Sil | 0.5 | — |
| FDC Blue No. 1 (.1%) | 0.3 | 0.3 |
| Perfume | 0.5 | 0.5 |
| D & C Yellow No. 11 (.1% alcohol) | 3.0 | 3.0 |
| | 100.0 | 100.0 |
| Appearance | Not stringy in consistency Bicarbonate separated overnight | Very viscous not stringy Unstable suspension |

These examples were prepared in accordance with the procedure defined in examples 1-3.

These suspensions are not pituitous and not stringy due to the high water content and low ethanol content despite the increased amount of hydroxyethyl cellulose suspending agent. Likewise, the addition of a second suspending agent did not overcome the inability to form a stable pituitous, stringy suspension.

These examples particularly point out the importance of a high alcohol and low water content in order to obtain a stable stringy suspension.

EXAMPLE 9

Example 2 is repeated except that the ethanol content is reduced to 60.40% and 0.05 Uvinul (ultraviolet absorber, 2,4 dihydroxy benzophenone) is added and the colors are replaced by 0.35% FDC Blue No. 1 (0.1% aqueous solution) and 0.3% D & C Yellow No. 10 (1.0% aqueous solution). This suspension is prepared in accordance with the procedure of Example 2 except that the Arlemol and Wickenol are preblended and heated and then added to the combination of Part 1 and 2, followed by the addition of the perfume, colors and brightener. This product is a viscous stable pituitous, stringy suspension with fast drying properties.

EXAMPLE 10

|      |                     |
|------|---------------------|
|      | Part I              |
| 15.0 | Distilled Water     |
| 10.0 | Propylene Glycol    |
| 0.4  | Natrosol 250 HR     |
|      | Part II             |
| 57.8 | Ethanol             |
| 10.0 | NaHCO$_3$           |
|      | Part III            |
| 1.0  | Wickenol            |
| 1.5  | Arlemol E           |
| 0.3  | FDC Blue No. 1      |
| 3.0  | D & C Yellow No. 11 |
| 0.5  | Perfume             |
| 99.5 |                     |

This composition is prepared in accordance with the procedure of examples 1–3.

Natrosol alone provides the stringy characteristics for suspending the Sodium Bicarbonate in the roll-on deodorant. The Cab-O-Sil of Examples 1–4, 6 and 9 optionally assists in dispersing the bicarbonate in the ethanol prior to its addition to Part I, but does not affect the production of the stringy pituitous suspension.

EXAMPLE 11

The composition of Example 10 was prepared in a sequential manner so that the bicarbonate is added to the water prior to the suspending agent as follows:

The water was added to the propylene glycol, followed by the bicarbonate and then the hydroxyethyl cellulose suspending agent and mixed. The alcohol is admixed followed by the Wickenol and Arlemol oils, colorants and perfumes, and the total composition is thoroughly mixed.

A curd type formation occurs due to the presence of lumps of hydroxyethyl cellulose which requires additional mixing to effect the stringy consistency in the suspension. This example shows that it is preferable, but not absolutely necessary, to add the bicarbonate to the water subsequent to the addition of the hydroxyethyl cellulose suspending agent, more specifically, to the clear viscous solution of hydroxyethyl cellulose in an alcoholic/aqueous media.

Other polyhydric alcohols can be substituted for propylene glycol in part or in total in the above Examples, such as glycerine, polypropylene glycol, etc. Similarly the ethanol can be replaced by other monohydric alcohols such as methanol or isopropyl alcohol. Likewise, other emollients can be substituted for the wheat germ glycerides and/or the polyoxypropylene stearyl ether such as isopropyl myristate or palmitate or any alcohol soluble oil.

All of the alcoholic/aqueous pituitous suspensions containing the bicarbonate have been found to be a highly effective deodorant, are stable, non-irritating, faster drying and the bicarbonate is delivered as a powder to be activated by the body moisture at the area of contact, such as underarm, foot, hand and any other sweat area. Potassium bicarbonate may be substituted for the sodium bicarbonate in part or in total in the above examples.

Although the present invention has been described and illustrated with reference to specific examples, it is understood that modifications and variations of composition and procedure are contemplated within the scope of the following claims.

I claim:

1. A fast-drying, stable viscous pituitous deodorant suspension comprising about 1–20% alkali metal bicarbonate particles uniformly suspended in a vehicle with substantially no bicarbonate in solution, comprising a high alcohol content of lower aliphatic monohydric alcohol and a low water content and hydroxyethyl cellulose suspending agent in an amount above its alcohol solubility and within the range of about 0.1–1%, said monohydric alcohol content exceeding the upper solubility level for the water soluble hydroxyethyl cellulose in said alcohol and within the range of about 55–75%, and the water content being sufficient to prevent precipitation of said suspending agent and at least 5%, if at least 10% polyhydric alcohol is also present in the suspension, and up to about 25% by weight.

2. The composition in accordance with claim 1, wherein the alkali metal bicarbonate is micropulverized sodium bicarbonate.

3. The composition in accordance with claim 1, containing a polyhydric alcohol in an amount not to exceed the monohydric alcohol content and sufficient to prevent precipitation of the suspending agent.

4. The composition of claim 3, wherein the polyhydric alcohol is selected from the group consisting of glycerine, propylene glycol and butylene glycol and polyglycols thereof.

5. The composition of claim 1, wherein the monohydric alcohol is selected from the group consisting of ethanol, methanol and isopropyl alcohol.

6. The composition of claim 1, containing non-volatile polar or non-polar ingredients selected from the group consisting of polyhydric alcohols and emollient oils.

7. The composition of claim 1, containing about 0.1–1% fumed silica as an additional suspending agent.

8. The method of making the viscous pituitous suspension of claim 1, which comprises preparing a clear viscous aqueous or aqueous alcoholic solution of hydroxyethyl cellulose heated to a temperature of about 130°–140° F., mixing this heated viscous solution with a monohydric alcoholic dispersion of the bicarbonate until a viscous pituitous suspension is formed with the bicarbonate particles uniformly suspended therein.

9. A method of deodorizing the human body comprising the application and deposition of a film of the composition of claim 1 which is activated by the sweat secretions to release the bicarbonate.

10. A method of deodorizing the human body comprising the application and deposition of an invisible film of the composition of claim 6 which is activated by the sweat secretions and controls the release of the bicarbonate.

* * * * *